United States Patent [19]

Kaye

[11] 4,355,897
[45] Oct. 26, 1982

[54] NEAR-SIMULTANEOUS MEASUREMENTS AT FORWARD AND BACK SCATTER ANGLES IN LIGHT SCATTERING PHOTOMETERS

[75] Inventor: Wilbur I. Kaye, Corona Del Mar, Calif.

[73] Assignee: Beckman Instruments, Inc., Fullerton, Calif.

[21] Appl. No.: 157,598

[22] Filed: Jun. 9, 1980

Related U.S. Application Data

[63] Continuation of Ser. No. 864,991, Dec. 27, 1977, abandoned.

[51] Int. Cl.$^3$ ............... G01N 21/01; G01N 21/49; G01N 21/85
[52] U.S. Cl. ................................ 356/338; 250/574; 356/342
[58] Field of Search ............... 356/301, 337, 338, 342; 250/574

[56] References Cited

U.S. PATENT DOCUMENTS

| | | | |
|---|---|---|---|
| 3,508,830 | 4/1970 | Hopkins et al. | 356/103 |
| 3,624,835 | 11/1971 | Wyatt | 356/103 |
| 3,843,268 | 10/1974 | Kaye | 250/574 X |
| 3,850,525 | 11/1974 | Kaye | 356/73 |
| 3,976,378 | 8/1976 | Pratt | 356/325 |
| 4,027,973 | 6/1977 | Kaye | 356/73 |
| 4,043,669 | 8/1977 | Gehatia et al. | 356/340 |
| 4,053,229 | 10/1977 | McCluney | 356/338 |

FOREIGN PATENT DOCUMENTS

| | | | |
|---|---|---|---|
| 938955 | 10/1963 | United Kingdom | 356/104 |
| 1298658 | 12/1972 | United Kingdom . | |

OTHER PUBLICATIONS

Smith, W. J., *Modern Optical Engineering*, pp. 128–129, McGraw-Hill, New York, 1966.
Kaye, W. I., Havlik, A. J., McDaniel, J. B., "Light Scattering Measurements on Liquids at Small Angles", Polymer Letters, vol. 9, pp. 695–699, (1971).
Kaye, W. I., Havlik, A. J., "Low Angle Laser Light Scattering-Absolute Calibration", Applied Optics, vol. 12, No. 3, pp. 541–550, (Mar. 1973).
Kaye, W. I., "Low-Angle Laser Light Scattering", Analytical Chemistry, vol. 45, No. 2, pp. 221A–225A, (Feb. 1973).
Kerker, M., *The Scattering of Light and Other Electromagnetic Radiation*, Chapter 8.2.1, (pp. 432–433), Academic Press, New York, (1969).
Nakagaka, M., Heller, W., "Theoretical Investigations on the Light Scattering of Colloidal Spheres VI Backward Scattering", J. Chem. Phys. 30, 783, (1959).
Benoit, Holtzer and Doty, J. Phys. Chem. 58, 635, (1954).
P. Kratochvil, *Light Scattering from Polymer Solutions*, Chapter 7, Academic Press, New York, (1972).

*Primary Examiner*—Bruce Y. Arnold
*Attorney, Agent, or Firm*—R. J. Steinmeyer; Robert R. Meads; John R. Shewmaker

[57] ABSTRACT

A light scattering photometer including a rotating segmented mirror intercepting light from a laser source and alternately directing the light into a sample zone along an optical axis in first and second opposite directions. A mask annulus coaxial with the optical axis intercepts light scattered from the sample in an incremental angle $\Delta\theta$ at a selected angle $\theta$ with respect to the axis. As the direction of sample illumination alternates, the annulus alternately intercepts forward scatter and back scatter of light from the sample at angles $\theta$ and $180° - \theta$, respectively, and passes the forward and back scatter in alternate succession to a detector. The detector output signal is demodulated to derive near-simultaneous forward and back scatter measurements from the sample. The photometer permits measurement at small values of $\theta$ approaching 0° and hence permits near-simultaneous scatter measurements at forward and back scatter angles spaced by an angle approaching 180°.

6 Claims, 4 Drawing Figures

NEAR-SIMULTANEOUS MEASUREMENTS AT FORWARD AND BACK SCATTER ANGLES IN LIGHT SCATTERING PHOTOMETERS

This is a continuation of application Ser. No. 864,991, now abandoned, filed Dec. 27, 1977.

BACKGROUND OF THE INVENTION

1. Field of the Invention

The present invention relates to light scattering photometers for making multiple measurements of light scattered from a sample and, more particularly, to a photometer permitting the near-simultaneous measurement of light scattered from a sample at forward and back angles of scatter.

2. Background of the Invention

I have described a laser light scattering photometer for measuring scattered light at selected angles and various improvements therein in the following references: (1) British Patent Specification No. 1,298,658, "Photometer for Measuring Total Radiant Energy at Selected Angles", published Dec. 6, 1972; (2) "Light Scattering Measurements on Liquids at Small Angles" by W. I. Kaye, A. J. Havlik, and J. B. McDaniel, Polymer Letters, Vol. 9, pp. 695–699 (1971); (3) "Low Angle Laser Light Scattering—Absolute Calibration" by W. I. Kaye and A. J. Havlik, Applied Optics, Vol. 12, No. 3, pp. 541–550 (March 1973); (4) "Low-Angle Laser Light Scattering" by W. I. Kaye, Analytical Chemistry, Vol. 45, No. 2, pp. 221A–225A (February 1973); (5) U.S. Pat. No. 4,027,973 (Kaye), "Detector Apparatus for Laser Light Scattering Photometers", filed July 2, 1973; (6) U.S. Pat. No. 3,843,268 (Kaye), "Sample Container for Laser Light Scattering Photometers", filed July 5, 1973; and (7) U.S. Pat. No. 3,850,525 (Kaye), "Simultaneous Multiple Measurements In Laser Photometers", filed July 9, 1973.

The foregoing reference all relate to a laser light scattering photometer which includes a laser light source the coherent light from which is focused by a lens onto a sample. Light scattered from the sample in an incremental angle $\Delta\theta$ at a forward angle $\theta$ is intercepted by a mask annulus and passed therethrough to a focusing lens. The light is focused by the lens into the aperture of a field stop and passes therethrough to a converging lens which converges the light to a photomultiplier detector. The detector provides a measure $P_\theta$ of the scattered light. The incident beam, suitably attenuated, is also transmitted through the sample and relayed to the detector to provide a measure $P_0$ of incident light. $P_\theta$ and $P_0$ are used to calculate the Rayleigh factor $R_\theta = P_\theta/(P_0\sigma L)$ where $P_\theta$ and $P_0$ are the radiant powers of the scattered and incident light beams, respectively; $\sigma$ is the solid angle of the detected scatter beam, and L is the length of the scattering volume parallel to the incident beam.

The foregoing photometer exhibits many desirable features for scattering measurements including small sample size, small angle measurements, low background, discrimination of scatter from interfering dust particles, and absolute calibration by measurement of geometric parameters. In this regard, the photometer permits reliable scatter intensity measurements on sample volumes as low as about $10^{-2}$ ml at a small forward scatter angle approaching 0°, e.g. in practice as small as about 1.5°. In calculating the Rayleigh factor from the above equation, the solid angle $\sigma$ is dictated by the dimensions of the mask annulus while the scattering volume path length L is dictated by the dimensions of the field stop. These parameters are geometrically measured; hence, the photometer measures the Rayleigh factor on an "absolute" basis providing absolute calibration of the photometer by the measurement of geometric parameters alone. In view of the small sample volume, there is less probability that interfering dust particles will be present in the scattering volume thereof. Moreover, because of the high power density within the small scattering volume, any dust particle which is present appears as a spike in the output scatter signal making its presence obvious. The extreme sensitivity of the photometer enables detection of scattering power $P_\theta$ infinitesimally less than the incident power $P_0$, typically less by a factor of $10^9$ or more, i.e. $P_\theta = P_0 \times 10^{-9}$. The laser photometer is described as particularly useful and applicable for measuring molecular weights and for detecting the presence of and measuring the size of particles in solutions or in air. The foregoing references are all specifically incorporated herein by reference as background regarding details of the light scattering environment in which the present invention resides.

It is known that the intensity of light scattered from a spherical particle is a function of both the scattering angle of the light and the refractive index of the particle relative to the dispersing medium in which it resides. Where the refractive index is known, the particle size may be determined from measuring Rayleigh scattering at a single scattering angle. Frequently, however, the refractive index is not known and for such cases measurements must be made at more than one scattering angle in order to determine particle size. If the particles to be measured are larger than the wavelength of the light used in the scattering measurement, it is advantageous to make the two scattering measurements at two relatively small angles. To this end, the aforementioned reference (7) discloses an arrangement for making simultaneous measurements for this purpose at two small and closely spaced angles. In reference (7), scattered light issuing from the sample in an incremental angle $\Delta\theta$ is partially intercepted by an elliptical mirror to segment the light into first and second incremental angular segments $\Delta\theta_1$ and $\Delta\theta_2$. Light within the respective first and second segments is directed simultaneously to respective first and second detectors. As disclosed, incremental angular segments $\Delta\theta_1$ and $\Delta\theta_2$ are adjacent, and hence closely spaced, angular segments at the forward scattering angle $\theta$.

While the foregoing procedure is satisfactory for measuring particles larger than the wavelength of light, it is generally unsatisfactory for measuring particles whose diameter is smaller than the wavelength of light used. This is because in the latter case the variation of scattered light intensity with scattering angle is small and, consequently, it is desirable to make measurements at two angles as widely spaced as possible to maximize the difference in measured scatter intensity at the two angles. Ideally, measurements would be desirable at two scattering angles spaced by an angle approaching 180°. By way of background, the measurement of the size of particles from the ratio of the scatter intensities at two angles symmetric about 90° has been done, and this ratio is called the dissymmetry. Reference is made to "The Scattering of Light and Other Electromagnetic Radiation" by M. Kerker, Academic Press, New York (1969) for a general discussion of this subject. When the two angles approach 0° and 180°, respectively, the ratio of intensities is called the extreme dissymmetry and is described in a paper entitled "Theoretical Investigations on the Light Scattering of Colloidal Spheres VI Backward Scattering" by M. Nakagaki and W. Heller, J. Chem. Phys. 30, 783 (1959). Heretofore, to my knowledge, no experimental measurements of extreme dissymmetry have been made because of the experimental and practical difficulties in making two satisfactory measurements at widely spaced scatter angles.

One practical difficulty in making particle scattering measurements at two spaced angles arises from the fact that the two measurements have to be obtained on the same particle, and the particle is often flowing through the light beam. For example, the photometer of references (1)-(7) is particularly adapted to make scattering measurements on a solution flowing through a sample zone into which the incident light is focused. If the particle size distribution in the solution is to be determined, scatter measurements at two spaced angles on as many particles as possible would be desirable. However, scatter measurements on a particle at two spaced angles are feasible only if they can be performed simultaneously or nearly simultaneously while the particle is in the path of the light beam.

Another area which would be benefited by near-simultaneous light scattering measurements at two spaced angles is the investigation of the polydispersity of dissolved macromolecules. Solutions of macromolecules are seldom monodisperse or all of one size and shape. A method for measuring polydispersity utilizing angular scattering data was developed by Benoit, Holtzer and Doty, J. Phys. Chem. 58, 635 (1954). The authors extrapolate low and high angle scattering intensity values to zero degrees and obtain weight and number average values of the solute molecular weight. Polydispersity can be determined from these two molecular weight averages. It can be shown that the extrapolation of the high angle data amounts to a single measurement at an angle approaching 180°. Hence, measurements at high and low angles give polydispersity information.

Moreover, if a macromolecular solution is separated into reasonably monodisperse fractions, light scattering measurements on each fraction at high and low scatter angles can be used to determine molecular shape or conformation. The low angle scattering intensity is a function of molecular weight only while the high angle data is a function of both molecular weight and shape. For a description of this theory see "Light Scattering from Polymer Solutions" P. Kratochvil, Chapter 7, Academic Press, New York (1972). The measurement of molecular shape in solution is of great importance, particularly for biopolymers. Gel permeation chromotography is a preferred technique for fractioning such samples.

In macromolecular solution study, the scatter of the solute is the parameter of interest and any particles in the solution add an interfering background scatter signal which must be distinguished from the solute scatter signal. The scatter intensity from an interfering particle may be typically one hundred times as great as the scatter intensity from the molecule of interest. If the solute were measured while motionless, the resulting signal could be either that of the solute or of an interfering particle motionless in the incident beam. Consequently, it would be desirable in this case also to flow the sample through the light beam so that interfering particles passing through the beam would appear as recognizable spikes in the scatter signal enabling discrimination between the solute and particle signals. Again, however, it is necessary to make the two angle measurements nearly-simultaneously on each flowing particle while the particle is in the path of the light beam.

The aforementioned reference (1) illustrates a laser photometer for measuring forward scatter from a sample and for separately measuring back scatter from a sample. in this regard, FIG. 1 of the reference illustrates an arrangement for measuring forward scatter at a forward angle approaching zero degrees, while FIG. 5 illustrates a modified arrangement for measuring back scatter at an angle approaching 180°. A second photometer for separately measuring forward and back scatter is illustrated in U.S. Pat. No. 4,043,669 (Gehatia et al.) for "Light Scattering Test Apparatus", filed May 28, 1976. This patent illustrates in FIG. 1 an arrangement for directing laser light through a sample and measuring forward scatter therefrom at a relatively large angle and illustrates, in FIG. 7, another arrangement for separately measuring back scatter from the sample. The latter arrangement requires that three mirrors and a rotating light chopper be rotated through 90° to convert the instrument from one for measuring forward scatter to one for measuring back scatter. Unfortunately, neither of the two foregoing photometers is adapted to make near-simultaneous measurements at forward and back angles of scatter.

SUMMARY OF THE INVENTION

The present invention resides in a light scattering photometer which overcomes the disadvantages of prior systems by permitting multiple measurements in a manner unattainable heretofore. The present photometer permits the near-simultaneous measurement of light scattered from a sample in forward and back directions. As a result, the photometer is ideally suited for obtaining information on the refractive index or size of particles or the polydispersity of dissolved macromolecules, particularly where samples to be studied are in motion or flowing through the light beam.

Briefly, the present photometer comprises a source of light, a sample zone having an optical axis along which light from the source passes to impinge upon and scatter from a sample in the sample zone, a detector, and means for intercepting light scattered from the sample at a predetermined angle $\theta$ with respect to the optical axis and for passing the intercepted light to the detector. In accordance with a primary aspect of the present invention, switching means alternately directs light from the source into the sample zone in first and second opposite directions along the optical axis to alternately illuminate a sample therein from opposite directions. In this manner light directed into the sample zone in the first direction is scattered from the sample and intercepted at the forward angle $\theta$, while light directed into the sample zone in the second direction is scattered and intercepted at the back angle $180° - \theta$. The intercepting means alternately passes the forward and back scatter to the detector. In the preferred embodiment, the switching means is a rotating mirror which alternately intercepts light from the source. Demodulation means synchronized with rotation of the mirror demodulates the output signal of the detector to derive both forward and back scatter information. In the foregoing manner, near-simultaneous measurements are derived at forward and back scatter angles which can approach 180° in separation.

DESCRIPTION OF THE PREFERRED EMBODIMENT

Figure 1:
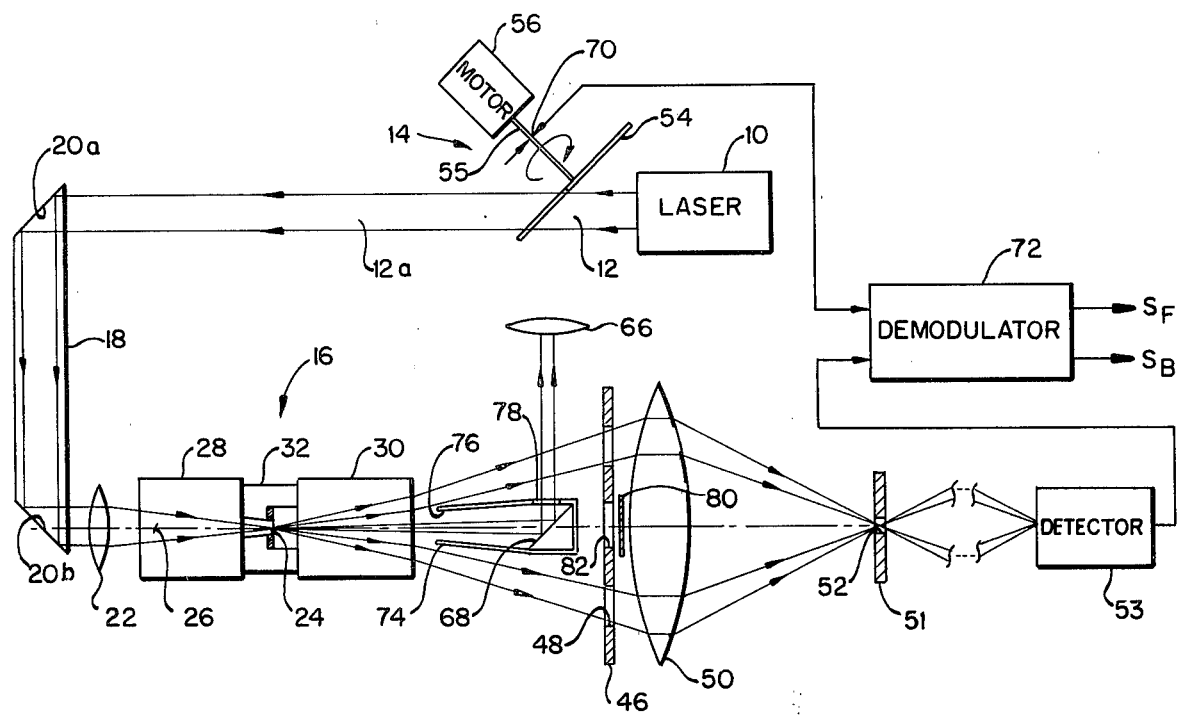
FIG. 1 is a generally cross-sectional view through optical elements of a light scattering photometer in accordance with the present invention. The figure illustrates light from a laser source directed into a sample zone in one direction, and depicts elements arranged to intercept light scattered from the sample at a forward scatter angle $\theta$.
Figure 2:
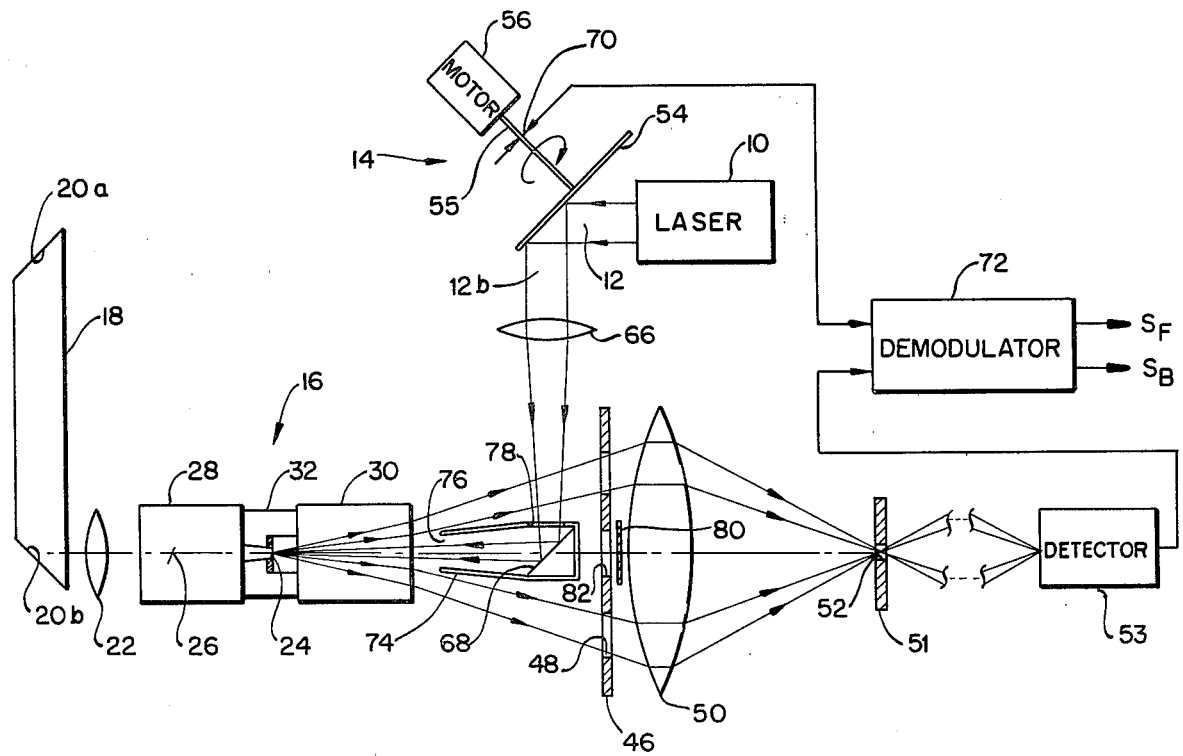
FIG. 2 is a view corresponding to that of FIG. 1 but illustrating light directed onto the sample zone in an opposite direction such that light scattered from the sample is intercepted at a back scatter angle $180° - \theta$.

As illustrated in FIGS. 1 and 2, the present invention is embodied in a light scattering photometer which includes a light source 10 generating a light beam defined by rays 12, and a light beam switching means, indicated generally by 14, for directing light from the source toward a sample container 16 to impinge upon and illuminate a sample contained therein. Preferably, light source 10 is a helium-neon laser operating in the TEM$_{00}$ mode. As illustrated in FIG. 1, light rays 12a passed by beam switching means 14 are redirected at end surfaces 20a and 20b of a prism 18 to a lens 22 or other light coverging device. The lens 22 functions to direct the light along an optical axis 26 extending through the sample container 16 and to focus the redirected light beam 12a to a minimum beam diameter at a point 24 on the optical axis within sample container 16.

Figure 3:
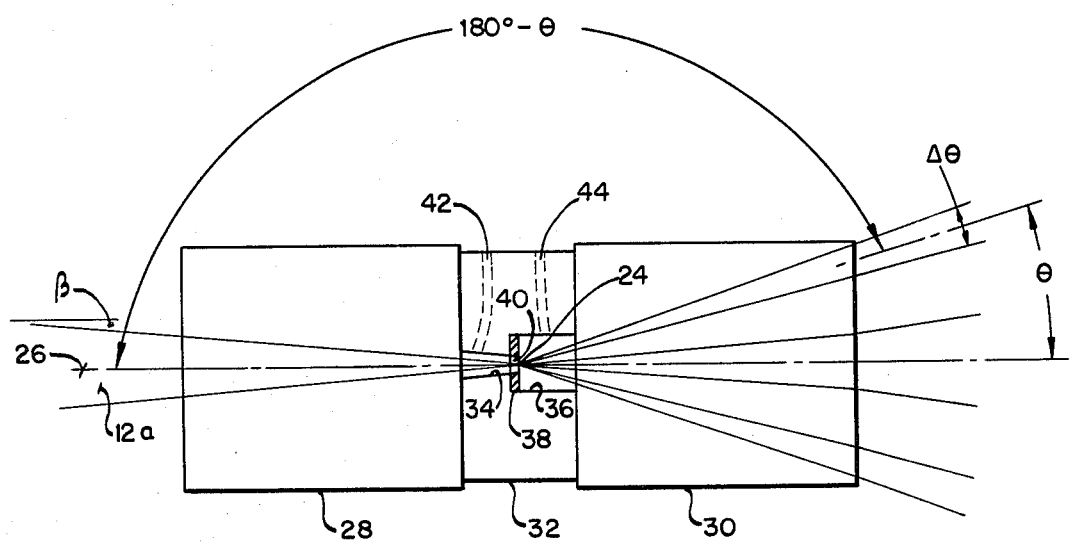
FIG. 3 is a cross-sectional view through a sample cell employed with the present photometer.

Sample container 16 may take the form illustrated in any of foregoing reference (1)–(7). FIG. 3 herein illustrates the improved container of reference (6) which includes first and second silica windows 28 and 30 spaced by a clear Teflon spacer 32 in the direction of optical axis 26. Spacer 32 includes two contiguous passageways 34 and 36 coaxial relative to the optical axis 26. Passageway 34 is frustoconical in shape while passageway 36 is cylindrical and joins passageway 34 at a plane normal to the optical axis and including the point 24. Preferably, a black glass disk 38 is disposed at the junction of the two passageways and includes an aperture 40 forming an extension of frustoconical passageway 34. The point 24 is preferably located within the aperture 40. Aperture 40 functions to intercept and block light scattered by lens 22 and by other optical components between container 16 and source 10 thereby preventing such extraneous light from passing through the system.

To allow for introduction of a sample into the measuring zone of the sample container 16, the spacer 32 further includes channels 42 and 44 intersecting passageways 34 and 36 respectively. Each channel may be fitted with a Leur fitting or similar device for connecting the channels to a sample source. Sample may be introduced intermittently or continuously into the sample zone through one channel and withdrawn through the other, as desired. It will be noted that the sample zone volume with such construction may be less than $10^{-2}$ ml so that both the sample volume and the scattering volume thereof are small. Attention is directed to the foregoing references for additional details regarding sample container construction.

As illustrated most clearly in FIG. 3, lens 22 focuses the light beam 12a to the point 24 at an angle of convergence $\beta$ with respect to the optial axis 26. The angle of convergence $\beta$ is generally small, e.g. as low as about 0.5°, since $2\beta$ is the smallest angle $\theta$ relative to the direction of incident beam 12a at which light scattered from a sample at point 24 may be intercepted for measurement without also intercepting a portion of the transmitted (i.e. non-scattered) incident beam. In this regard, and as further illustrated in FIG. 3, the present photometer is adapted to intercept and measure light scattered from the sample zone of container 16 in an incremental angle $\Delta\theta$ at a predetermined and selectable angle $\theta$ with respect to the optical axis 26. For incident light rays 12a, which travel from left to right in FIG. 3, angle $\theta$ defines a forward scatter angle which, as taught in the aforementioned references, may approach 0°, and in practice reach a value as small as about 1.5°.

The optical arrangement for intercepting light scattered by a sample corresponds to that of the aforementioned references and includes, referring to FIGS. 1 and 2, a mask 46 having an annular aperture 48 therein coaxial with optical axis 26. Aperture 48 is oriented to intercept all light energy scattered from the sample zone in the incremental angle $\Delta\theta$ at selectable angle $\theta$ relative to the optical axis 26. Thus arranged, the intercepted light is defined by a conical surface having an apex at point 24 and a base formed by aperture 48. The scattered light thus intercepted by annular aperture 48 is passed to a focusing lens 50 or other light converging device which focuses the light into an aperture 52 of a field stop 51. Annulus 48, lens 50, and aperture 52 combine to admit through aperture 52 only light issuing from the sample at angle $\theta$ in incremental angle $\Delta\theta$ and to essentially eliminate other undesired light. Moreover, the scattering volume of the sample is determined by the diameter of the incident laser beam, by the dimension of annulus 48, and by the diameter of field stop aperture 52. In this regard for a sample volume in passageways 34 and 36 of container 16 on the order of $10^{-2}$ ml, the corresponding scattering volume thereof may be several orders less, e.g. on the order of $10^{-5}$ ml.

Light passing through aperture 52 in field stop 51 is passed to a lens or other conventional converging device (not shown) which converges the light to a detector 53, preferably a photomultiplier tube as taught in the aforementioned references. For ease of illustration, the rays diverging from aperture 52 and converging toward detector 53 are broken to shorten the illustrated optical path length. The detector 53 is preferably of the improved construction illustrated in reference (5).

Figure 4:
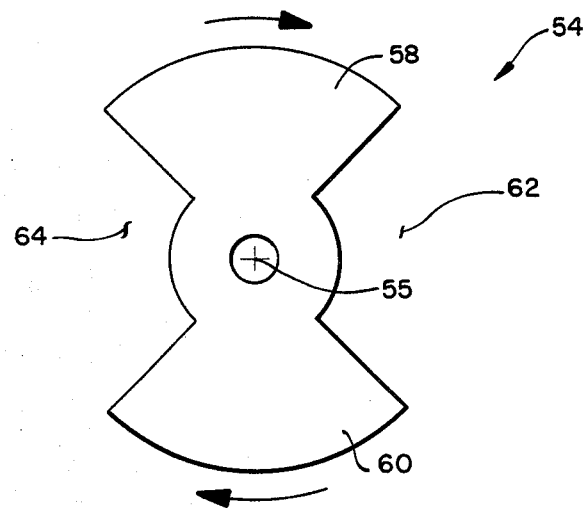
FIG. 4 is a front elevational view of a rotating mirror employed in the photometer of FIGS. 1 and 2.

Except for beam switching means 14, the photometer as described to this point corresponds essentially in strucure and operation to that described in the Background of the present specification. Thus, as described, the laser light 12a focused by lens 22 into the sample zone of container 16 and scattering from sample therein in an incremental angle $\Delta\theta$ at a forward scatter angle $\theta$ is intercepted by annulus 48 and passed to detector 53 for measurement. As indicated previously, in addition to the thus derived forward scatter information on the sample, it is desirable to simultaneously obtain back scatter information on the same sample. To this end, and in accordance with a primary aspect to the present invention, the beam switching means 14 is provided to alternately direct the light rays 12 from source 10 into the sample zone in opposite directions along optical axis 26. To accomplish this, one form of the switching means 14 comprises a segmented mirror 54 coupled to drive shaft 55 of a drive motor 56 to be rotated thereby to intercept the light rays 12 generated by the laser source 10. Mirror 54 includes alternate reflecting and open segments and is disposed such that the mirror segments thereof intercept light rays 12 from source 10 at a 45° angle. FIG. 4 illustrates one form of such a segmented mirror which includes first and second reflective mirror segments 58 and 60 separated by open segments 62 and 64.

The photometer further includes a focusing lens or other light converging device 66 and a mirror or other light redirecting device 68. Mirror 68 is situated on and at 45° with respect to optical axis 26 between the sample container 16 and mask annulus 46.

With rotating mirror 54 so disposed in the path of light beam 12 and rotated by motor 56, the light beam is alternately intercepted by a reflective segment 58 or 60 and then by an open segment 62 or 64 of the mirror. When intercepted by an open segment, light rays 12a are passed therethrough to prism 18 and focusing lens 22 in the manner heretofore described and as illustrated in FIG. 1. Alternately, as illustrated in FIG. 2, when beam 12 is intercepted by a reflective mirror segment 58 or 60, the rays 12b thus intercepted are directed downwardly in the figure through focusing lens 66 onto mirror 68. Mirror 68 redirects the focused light along the optical axis 26 to focal point 24 within the sample container 16 but in a direction of incidence along axis 26 opposite to that of FIG. 1. For such oppositely directed light, annulus 48 in mask 46 intercepts back scatter of light from the sample in the same incremental angle $\Delta\theta$ but at a back scatter angle of $180° - \theta$. Consequently, as the open and reflective segments of rotating mirror 54 alternately intercept light beam 12, the beam is alternately switched and directed into the sample zone from opposite directions along the optical axis 26. Consequently, annulus 48 intercepts in alternate succession, and in near simultaneity, forward scatter at angle $\theta$ and back scatter at angle $180° - \theta$ and passes such forward and back scatter alternately to detector 52. In turn, detector 52 generates an output signal which, in a first interval, represents a measure of forward scatter intensity and which, in a second interval, represents a measure of back scatter intensity.

The detector output signal is demodulated to separate the forward and back scatter information therein. For this purpose, the rotational position of the drive shaft of motor 56 is monitored by a commutator 70 and is supplied as a first input to a conventional demodulator 72, while the output of detector 52 is supplied as a second input thereto. Demodulator 72, in turn, generates first and second output signals $S_F$ and $S_B$ representing, respectively, the forward and back scatter intensity information. It is apparent that the time interval between forward and back scatter measurements will depend on the rotational speed of the mirror 54 and will provide an essentially near-simultaneous measurement of the forward and back scatter. As a result, the photometer of the invention is ideally suited for measuring sample particles which are in motion or otherwise flowing through the incident light beam and for which near-simultaneous forward and back scatter measurements are desired on the same particle.

The switching frequency of the rotating mirror 54 will depend upon the type of sample being measured and the rate of motion or flow of the sample and associated particles through the incident light beam. For some samples, particles may remain in the path of the beam for an interval of several seconds, and for such particles a relatively slow switching frequency of 10 Hz would be satisfactory. In some cases, however, a particle will be in the path of the beam for only millisecond or microsecond intervals. In such case a much higher switching frequency is required to insure that all particles passing through the beam are actually detected. Since there is a practical upper limit to the speed of rotation of segmented mirror 54, further increases in switching frequency may be attained by increasing the number of reflective and open segments of the mirror. Thus, the mirror could take the form of a circular disk having a plurality of radial notches around its periphery forming open segments alternating with reflective segments. For a disk having 100 reflective and 100 open segments and rotated at 3600 rpm, a switching frequency of approximately 6 kHz would result.

It will be noted that when an open segment 62 or 64 in rotating mirror 54 intercepts light beam 12, the rays 12a are folded by prism 18 and focused by lens 22 into the sample zone as previously described. Light which is not scattered by the sample and which exits window 30 along the optical axis 26 is intercepted by mirror 68 and directed thereby toward lens 66 which relays the light into the same open segment in the rotating mirror. Such light is passed through the open segment and dissipated on the walls (now shown) of the photometer housing.

Alternatively, when a reflective segment 58 or 60 of mirror 54 intercepts light beam 12 and directs the light rays 12b downwardly and into the sample zone in the opposite direction, light which is not scattered by the sample exits window 28 along optical axis 26 (to the left in FIG. 2). Such light is directed by lens 22 and prism 18 onto the back surface of the same reflective mirror segment where it is dissipated.

As shown in FIGS. 1 and 2, the deflecting mirror 68 is housed within a light shielding structure 74. Structure 74 functions to prevent rays scattered by mirror 68 from illuminating the end face of window 30 in the vicinity of the exiting back scatter from the sample within incremental angle $\Delta\theta$. To this end, shield 74 comprises a generally frustoconical housing axially aligned on optical axis 26 and having a first window area 76 on optical axis 26 adjacent sample container window 30 and a second window area 78 in a side wall thereof for passing light to and from the reflecting surface 68 at 90° with respect to axis 26. Any light reflected from mirror 68 which would otherwise strike the end face of the sample container window 30 in the vicinity of the back scatter is intercepted by the interior conical wall of the shield 74 and thereby precluded from striking the window and hence from scattering or reflecting therefrom. This minimizes end window reflections which could otherwise be intercepted by annulus 48 and thereby introduce an undesirable background signal on the back scatter signal itself.

When it is desired to measure the incident light, i.e. the non-scattered light exiting sample container window 30 along optical axis 26, the mirror 68 and associated shielding structure 74 are removed and the light is permitted to pass through a central aperture 82 in mask 46, and through a safety attenuator 80 to lens 50. The light is relayed therefrom to the detector 53 which provides a measure of the incident light $P_0$ for calculating the Rayleigh factor in the manner previously described. Attenuator 80 is provided to prevent damage to equipment and injury to personnel when the mirror and shielding structure are removed. Additional attenuators (not shown) are provided for insertion into the beam path between source 10 and sample container 16 when mirror 68 and shield 74 are removed. Since the incident beam intensity exceeds the scatter intensity typically by a factor of $10^9$ or more, the attenuators are calibrated to proportionately reduce the intensity of the incident beam, when measuring non-scattered light, to approximate the value of the beam intensity when measuring scatter intensity.

It will be evident from the foregoing that the present invention provides a simple and straightforward photometer for making near-simultaneous forward and back scatter measurements on a sample in a manner heretofore unobtainable. As angle $\theta$ approaches 0°, the separation between the forward and back scattering angles approaches 180° thereby providing a powerful tool for the study of particle refractive index and dissolved macromolecular polydispersity. The invention is compatible with prior photometer arrangements and in conjunction therewith provides an array of analytical hardware and techniques to researchers and industry for significantly improved light scattering investigations. While a preferred embodiment of the invention has been illustrated and described, it will be appreciated that modifications may be made therein without departing from the scope of the invention as defined by the appended claims.

What is claimed is:

1. A light scattering photometer comprising:

a source of light;

a sample zone having an optical axis along which light from the source passes to impinge upon and scatter from a sample in the sample zone;

a detector;

means for intercepting light scattered from the sample at a predetermined angle $\theta$ with respect to the optical axis and for passing same to the detector;

switching means for alternately directing light from the source into the sample zone in first and second opposite directions along the optical axis to illuminate a sample therein in alternate succession and in near-simultaneity from said opposite directions such that for light directed into the sample zone in said first direction the intercepting means intercepts forward scatter from the sample at said angle $\theta$ while for light directed into the sample zone in said second direction the intercepting means intercepts back scatter from the sample at an angle $180° - \theta$, the intercepting means passing said forward scatter and said back scatter in alternate succession and in near-simultaneity to the detector; and demodulation means synchronized with the alternation of said switching means for demodulating the output of said detector to derive near-simultaneous forward and back scatter measurements from the sample.

2. The photometer of claim 1 wherein the switching means alternates at a frequency in the range 10 Hz–6 kHz.

3. In a laser light scattering photometer of the type including means for focusing light from a laser source into a sample zone, means for intercepting a cone of light issuing from the sample in an incremental angle $\Delta\theta$ at an angle $\theta$, means for focusing the cone of light into the aperture of a field stop, and detector means for measuring the light passing through said aperture, the improvement comprising:

means for alternately directing focused light from the source into the sample zone in first and second opposite directions along an optical axis therethrough to illuminate a sample therein in alternate succession and in near-simultaneity from said opposite directions such that for light directed into the sample zone in said first direction the intercepting means intercepts forward scatter from the sample at said angle $\theta$ while for light directed into the sample zone in said second direction the intercepting means intercepts back scatter from the sample at an angle $180° - \theta$, said intercepting means passing said forward scatter and said back scatter in alternate succession and in near-simultaneity to said detector means; and demodulation means, synchronized with the alternation of said directing means, for demodulating the output of said detector means to derive near-simultaneous forward and back scatter measurements from the sample.

4. The photometer of claim 3 further comprising light shielding means along said optical axis and through which said focused light is directed in said second direction and which intercepts and blocks any interfering scattering of said focused light.

5. The photometer of claim 4 wherein said light shielding means is frustoconical.

6. The photometer of claim 3 wherein the directing means alternates at a frequency in the range 10 Hz–6 kHz.

* * * * *